DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JUNE 22, 1971

887 O.G. 1046

T887,023

PREPARATION OF BIS(CHLOROFORMATES) OF 2,2,4,4-TETRAALKYL-1,3-CYCLOBUTANEDIOLS

Raymond D. Clark, P.O. Box 511,
Kingsport, Tenn. 37662

Filed May 13, 1970, Ser. No. 36,998
Int. Cl. C07c *69/64*
U.S. Cl. 260—463
No Drawing. 11 Pages Specification

Process for the preparation of bis(chloroformates) of cyclic secondary glycols such as those of the 2,2,4,4-tetraalkyl-1,3-cyclobutanediol series by reaction between the glycol and phosgene employing a Lewis base such as pyridine as the catalyst. These compounds are useful as chemical intermediates for the preparation of various polymeric products such as polyurethanes, polycarbonates, synthetic lubricants and plasticizers with high hydrolytic stability. In this reaction an equivalent amount of hydrogen chloride gas is evolved. The process is distinguished from known processes of preparing bis(chloroformates) by the fact that only a catalytic amount of a Lewis base is employed as distinguished from the use of an equivalent amount of a base or use of no catalyst. By catalyzing the reaction in this manner a substantial improvement in yields of the bis(chloroformate) product is obtained, as compared to the yields obtained from known processes where no catalyst is employed, and the necessity for removing an equivalent amount of salt from the product is avoided.